United States Patent [19]

Schubert et al.

[11] Patent Number: 4,483,666
[45] Date of Patent: Nov. 20, 1984

[54] HOSE PUMP FOR MEDICAL USES

[75] Inventors: Ernst W. Schubert, Lübeck; Josef Dörfler, Melsungen, both of Fed. Rep. of Germany

[73] Assignee: Intermedicat GmbH, Emmenbrucke, Switzerland

[21] Appl. No.: 515,118

[22] Filed: Jul. 19, 1983

[30] Foreign Application Priority Data

Jul. 20, 1982 [DE] Fed. Rep. of Germany ....... 3227051

[51] Int. Cl.³ ............................................. F04B 43/08
[52] U.S. Cl. .................................. 418/45; 417/474; 417/475; 417/476; 418/50
[58] Field of Search ........................ 417/474, 475, 476; 418/45, 49, 50; 404/153

[56] References Cited

U.S. PATENT DOCUMENTS 2,752,852 7/1956 Offutt ............................ 418/45 UX
2,958,294 11/1960 Johnson ............................ 418/45
3,669,578 6/1972 Nameny ............................ 418/45

Primary Examiner—Richard E. Gluck
Attorney, Agent, or Firm—Kenyon & Kenyon

[57] ABSTRACT

A hose pump comprises a housing in which a drive shaft is mounted. The shaft is provided with an obliquely extending shaft piece on which a swash plate is mounted. The swash plate end face presses against a hose which lies in an annular groove located in the underside of the housing cover. The swash plate does not substantially rotate relative to the housing or to the hose and therefore exerts substantially no shear on the hose.

21 Claims, 6 Drawing Figures

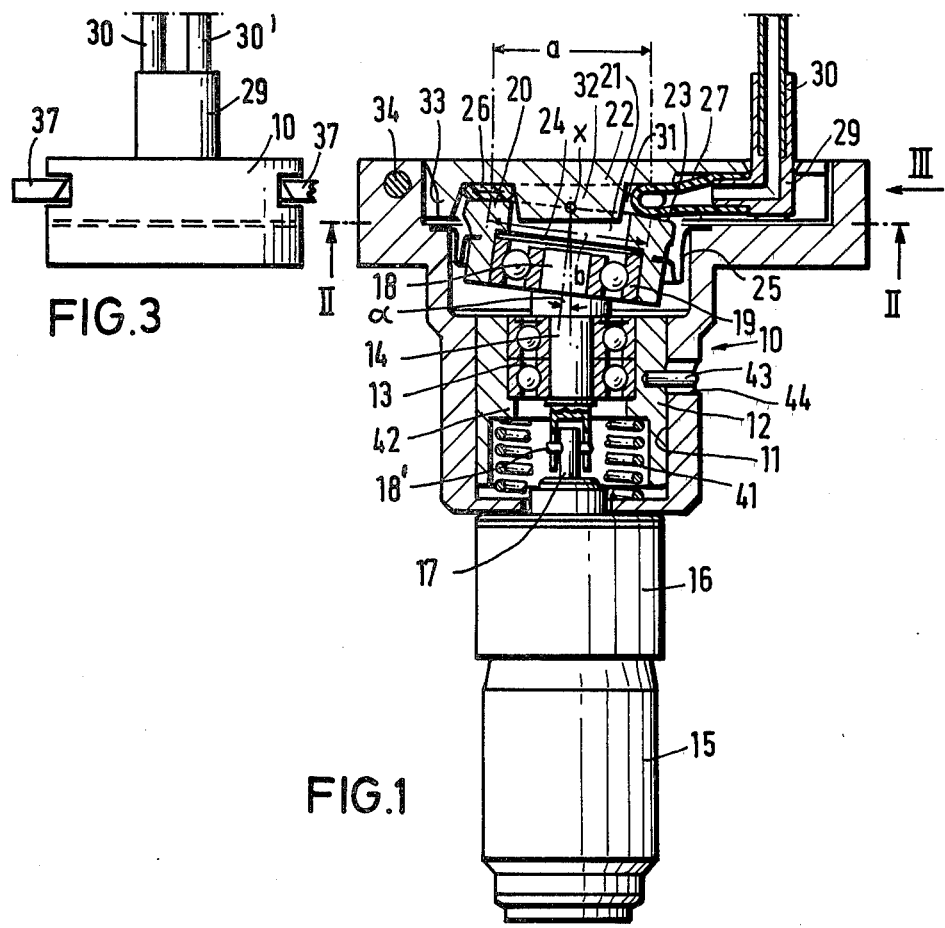
FIG.3
FIG.1
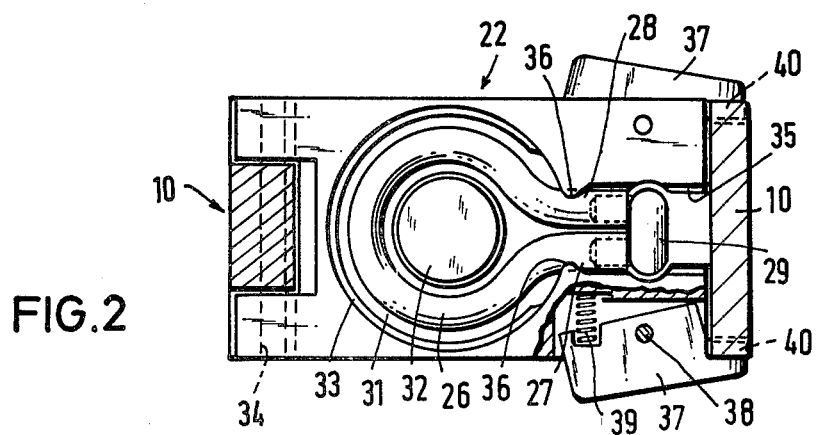
FIG.2

HOSE PUMP FOR MEDICAL USES

FIELD OF INVENTION

This invention relates to a hose pump. More particularly, this invention relates to a hose pump for medical uses.

BACKGROUND OF THE INVENTION

The supplying of liquids into the body of medical patients is effected in many instances from a supply vessel from which the liquid runs out by the influence of gravity. If a higher precision in the rate at which liquid is supplied is required, or if the delivery pressure from gravity is not sufficient, positive-displacement pumps are used. The structural parts of such pumps which come in contact with the liquids are, as a rule, made of plastic articles intended for a single use and which are discarded after such use. These plastic articles should be easy and inexpensive to manufacture. In addition, they should ensure the medically necessary precision and safety.

U.S. Pat. No. 2,915,983 discloses a hose pump wherein a drive shaft is mounted in a housing. The drive shaft has at its end an eccentrially arranged shaft piece extending at an angle. On this shaft piece, a swash plate is mounted which is secured against rotation relative to the housing of the hose pump. Between the swash plate and a cover which closes the housing, a hose section laid in rings is arranged. The ends of the hose section are passed through slots in the cover. The hose ends are brought out of the cover and are connected with a liquid source and with a user. When the drive shaft rotates, the swash plate is caused to wobble, pressing a region of the annular hose section against the cover and squeezing it flat. The flattened region moves during the wobble motion, so that the liquid contained in the annular hose section is pushed forward in the hose.

Hose pumps of the prior art have the disadvantage that insertion of the hose is difficult and requires a certain skill. A section of the hose must be laid in the cover or respectively over the swash plate in rings, while the very long ends are brought out of openings in the cover. The diameter of the annular hose section is not fixed, so that the position of the annular hose section in the hose pump is undefined. If the diameter of this annular hose section is made too large or too small, relative movements between the annular hose section on the one hand and the cover or swash plate on the other hand will occur during the revolving squeezing by the swash plate. These relative movements lead to increased friction and to wear and loss of output. In addition with the hose pumps of the prior art, the insertion of the hose requires a certain degree of experience. If the hose is inserted the wrong way, the pump will deliver in the wrong direction.

Also known, is a hose pump (U.S. Pat. No. 3,720,489) where a swash plate forms the cover of the housing. The annular hose section is installed in an annular groove in the housing. The swash plate is pressed in the direction of the annular groove by a spring. In this hose pump also, the hose may be inserted in any direction with the possibility of connecting the long hose ends protruding from the housing in any manner. This hose pump also does not provide for simple changing of the hose and does not ensure that the hose can be inserted only in a defined position in order to avoid unintended reversal of the delivering direction.

For medical uses, where the hose pump is to deliver, for example, blood or a serum, the hose is used as a disposable or throw-away article. Therefore, it must be easy to remove the hose from the pump and to replace it. Since incorrect insertion of the hose may, in such applications, have serious consequences for the patient, it must be assured that operation of the hose pump is possible only with the hose inserted correctly.

OBJECT OF THE INVENTION

It is therefore an object of the present invention to provide a hose pump, particularly for medical uses, where the hose can be replaced in a simple manner and which can be handled without problems, for instance, by the nursing personnel of a hospital or the patient.

These and other objects of the present invention will become apparent from the following description and claims in conjunction with the drawings.

SUMMARY OF THE INVENTION

In accordance with the present invention, the cover of the hose pump has on its underside an annular groove for securing the annular hose section as well as a clamping means for fixing the hose in the cover. The hose ends are connected with a common coupling piece which is insertable in the cover and has inflow and outflow connections. On the side of the cover opposite the coupling piece, the cover is connected with the housing by a hinge. A locking device is arranged near the coupling piece for locking the cover in the closed position on the housing.

BRIEF DESCRIPTION OF THE DRAWINGS

In the drawings forming part hereof:

FIG. 1 is a longitudinal sectional view through a hose pump in accordance with one embodiment of the present invention;

FIG. 2 is a view along line II—II of FIG. 1;

FIG. 3 is a partial schematic front view of the hose pump of the invention from the direction of arrow III in FIG. 1;

DESCRIPTION OF THE PREFERRED EMBODIMENTS

Figure 2A:
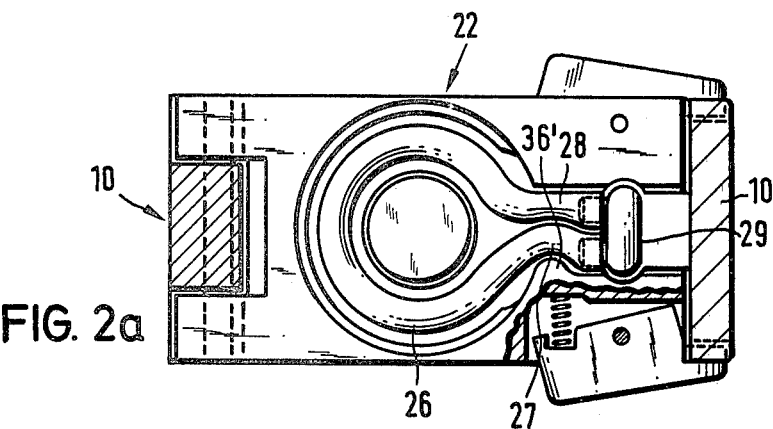
FIG. 2a is a schematic view of a modified embodiment of the invention as illustrated in FIG. 2.

In order to provide a more complete understanding of the present invention and an appreciation of its advantages, a description of the preferred embodiments is presented below.

In the hose pump according to the invention, and with reference to FIG. 1 and FIG. 2, both ends of the hose 26 are connected with a common coupling piece 29 which is inserted together with the hose 26 in a recess or annular groove 31 in the cover 22 of the hose pump. Thus the hose 26 together with the coupling piece 29 forms a throw-away unit. The coupling piece 29 assures that the hose 26 is inserted in the cover 22 in the correct position and direction of delivery. Changing the hose 26 is done after the cover 22 has been flapped up about the hinge 34. Changing the hose 26 merely requires simple manipulations. A locking device 37 is released and the cover 22 flapped up. Then the hose 26, together with the coupling piece 29, is removed from the cover 22 and replaced by a new hose and coupling piece. The annular groove 31 brings about the exact positioning of the annular hose section 26 in the cover 22, so that no major displacements of the hose 26 occur in operation. In particular, frictional stress in the circumferential direction of the hose is avoided. Insertion of the hose is facilitated by the pivotable mounting arrangement of the cover on the housing. The cover 22 is captive and is guided exactly during the closing movement. Therefore, shifting of the hose and wedging of the hose during closing of the cover is avoided.

In hose pumps, the danger exists that delivery may stop briefly, so that even a drawing back of the liquid occurs if the squeezing element passes over the outlet-side end of the hose and this end does not subsequently regain the full hose cross-section. To avoid or at least to reduce the discontinuities caused during the delivery, in accordance with the present invention, two hoses may be arranged side by side in a plane with each hose 26 having its own swash plate 20 assigned to it. (See FIGS. 4 and 5). The swash plates 20 are driven by a common drive at equal speeds, and the two hoses share a common coupling piece 29 having a single inflow and a single outflow. In this way, two hose pumps are combined in such a manner that their hoses together with the coupling piece form a single throw-away or disposable unit. The two hoses may be arranged in a common cover. The swash plates 20 of the two hoses are driven phase-shifted or in phase opposition, so that the critical phases of the brief interruption of the delivery do not coincide.

In the following, the illustrative embodiments of the invention are explained in greater detail with reference to the drawings.

The hose pump illustrated in FIGS. 1 to 3 comprises a housing 10 with a cylindrical bore 11, in which a sleeve 12 is mounted for lengthwise displacement. In the interior of sleeve 12, ball bearings 13 support the shaft 14, which is driven by an electric motor 15 through a reduction gear 16. The drive shaft 17 is formed by the output shaft of the reduction gear 16, and it is coupled with shaft 14 via a fork type coupling 18' in such a way that shaft 14 can execute small axial displacements relative to the output shaft 17.

At its output end, shaft 14 has an angularly bent shaft piece 18, the axis of which forms with the axis of shaft 14 an acute angle alpha ("α"). The swash plate 20 is mounted on this shaft piece 18 through a ball bearing 19. Ball bearing 19 and swash plate 20 are contained in a chamber 21 inside the housing 10. This chamber can be closed with the cover 22. In the present embodiment, the swash plate 20 comprises a ring, the outer end face 23 of which is beveled to match the angle alpha. The intersection of the axes of shaft 14 and shaft piece 18 lies in the plane of the mean diameter "b" of the end face 23 (i.e. of the diameter of the median circle of the conical surface of the end face 23).

The ball bearing 19 is mounted in the interior of the ring, the outer end face of which is sealed by a seal disk 24, so that no liquid can penetrate through the axial channel of the swash plate 20. The inner edge of a membrane 25 is fastened at the circumference of the swash plate 20. The outer edge of membrane 25 is fastened on the sidewall of chamber 21 of housing 10. Thus, the seal disk 24 together with the membrane 25 forms a liquid-proof seal between the drive mechanism of swash plate 20 against the space receiving the hose 26.

Hose 26 is attached to the underside of cover 22. With reference to FIG. 2, hose 26 is bent or curved in the form of a ring, with the inlet 27 and the outlet 28 being arranged side by side and extending out radially with respect to the ring. Inlet 27 and outlet 28 are connected with a coupling piece 29 of essentially L-shaped or angle form, whose inflow nipple 30 and outflow nipple 30' protrude from the cover 22 vertically.

Hose 26 is inserted in an annular groove 31 on the underside of cover 22. This annular groove 31 is limited internally by an axially raised projection 32 and externally by a circling edge 33 of equal depth. As can be seen from FIG. 1, the annular swash plate 20 engages into the annular groove 31 of cover 22. The depth of penetration of swash plate 20 into groove 31 varies over the circumference because of the oblique position of swash plate 20. Hose 26 is squeezed together in the axial direction between the outer face 23 of the swash plate 20 and the bottom of the annular groove 31.

With reference to FIG. 1, the mean diameter "a" of the annular end face 23 of swash plate 20 is the same as the mean diameter "b" of the annular groove 31 which in turn is the mean diameter of the hose ring installed in groove 31. As a result, the end face 23 executes a pure rolling movement in groove 31, but without turning in this groove. If the mean diameters "a" and "b" are different, the swash plate 20 would tend to revolve slowly in the housing about the shaft piece 18. In so doing it would exert a shearing action on the hose 26, and this would cause friction losses which reduce the efficiency.

Cover 22 is fastened to housing 10 by a hinge 34, so that it can be flapped or pivoted open according to FIG. 2. The coupling piece 29 is located at the end of cover 22 opposite to the hinge 34. At this end an oblong slot 35 is provided. The hose 26, inserted in cover 22 from below, is retained by fishplates 36 which partly span the inlet-side end and the outlet-side end of hose 26. Between these fishplates 36, however, there is a gap which is wide enough for the hose 26 to be taken out of cover 22 with relatively slight deformation.

The embodiment of the invention illustrated in FIG. 2a corresponds to a large extent to that of FIG. 2. The only difference is that instead of the fishplates 36, which according to FIG. 2 retain the hose 26 in the cover, there is provided at the edge of the oblong slot 35 in cover 22 a semi-cylindrical bulge 36' which presses one hose end near the coupling piece 29 in the direction of the other hose end. The hose is thus deformed, both hose ends being slightly compressed and retained in cover 22 by clamping type action.

To lock the cover 22 in the closed position in the housing 10, claws 37 are provided at the end of cover 22 opposite to hinge 34. These claws 37 are mounted by a hinge pin 38 on cover 22 and are pressed into the locking position by a spring 39. As illustrated in FIG. 2 and FIG. 3, their outer ends 40 engage in lateral recesses in housing 10 to lock cover 22 to housing 10 in the closed position. By laterally pressing in the claws 37, their ends 40 are spread apart with the springs 39 being compressed. The cover 22 is thereby unlocked from the housing 10 and can be lifted up.

To place the hose pump into use, first hose 26 together with the coupling piece 29 is inserted in cover 22 in the manner shown in FIG. 2. Then, cover 22 is closed and locked on housing 10. As a result, the swash plate 20 is pressed against hose 26 in its farthest protruding region so firmly that it pinches the hose 26 in the annular groove 31. A single nip forms along the circumference of the ring formed by hose 26. This nip is sufficiently long in the circumferential direction that no short circuit develops at the inlet and outlet. Briefly, both hose ends 27 and 28 are pinched jointly. When motor 15 is turned on, shaft 14 rotates and swash plate 20 executes a wobble motion, but without participating in the rotation. Due to the wobble motion, the point at which maximum compression of hose 26 takes place circles along the ring formed by hose 26 at constant speed. In this way, the liquid contained in hose 26 is pushed forward from the inlet 27 to the outlet 28.

After use, the claws 37 are released and cover 22 flapped up. The hose 26 together with the coupling piece 29 can then be removed and replaced.

The ball bearings 13 and 19 for supporting shaft 14 and swash plate 20 respectively not only serve as radial ball bearings but are also able to transmit axial forces. Accordingly, the bearing pressure of spring 41 is transmitted to swash plate 20. Spring 41 is supported on the rear end wall of housing 10 and presses against a ring shoulder 42 of sleeve 12, so that sleeve 12 together with shaft 14 and the ball bearings 13 and 19 as well as the swash plate 20 are pressed in the direction of hose 26 or cover 22 by the force of compressed spring 41. In order to secure sleeve 12 nonrotationally in housing 10, a radially projecting pin 43 extends through an axial slot 44 in the wall of housing 10 and into a bore provided in sleeve 12. Pin 43 serves also as axial stop, so that the swash plate 30 will not fall out of the housing 10 when the cover is open. In addition, when the cover is closed without a hose placed in groove 31, pin 43 prevents swash plate 20 from coming in contact with the guides 32 and 33 and causing damage.

Since that part of the swash plate 20 which projects axially farthest forward and causes the maximum pinching of the hose 26 revolves on the circle formed by the hose, liquid is transported from the inlet 27 to the outlet 28.

Figure 4:
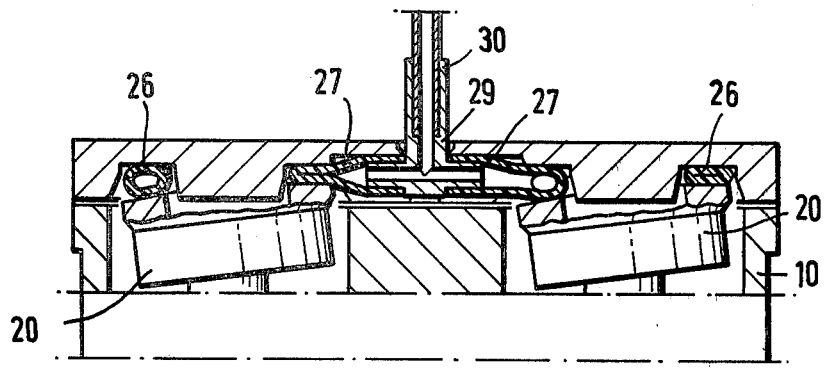
FIG. 4 is a schematic longitudinal sectional view through the working part of a double hose pump in accordance with another embodiment of the present invention; and, FIG. 5 is a schematic view of the cover of the double hose pump illustrated in FIG. 4 in the open state with the hoses inserted.
Figure 5:
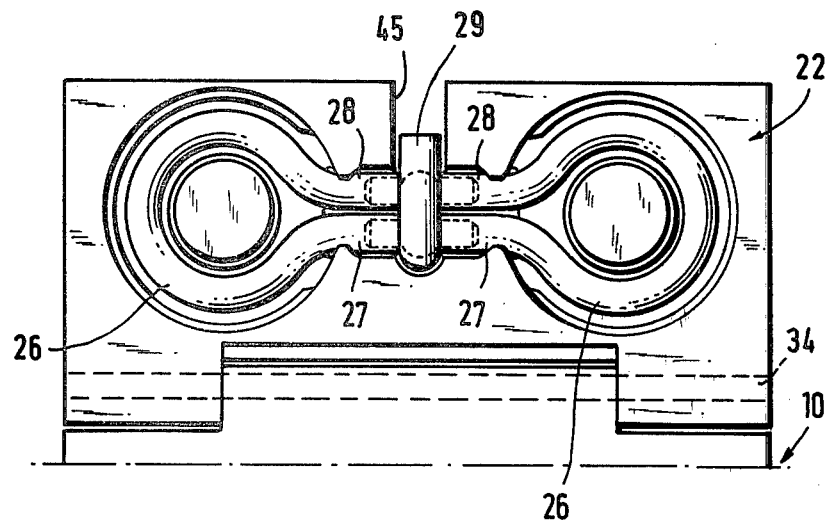

In the embodiment illustrated in FIGS. 4 and 5, two hose pumps are arranged side by side in a common housing 10. The swash plates 20 of both hose pumps are driven in opposite directions and their inlets 27 are connected with one another, as are also their outlets 28. Preferably, both swash plates are driven each at the same speed most suitably by a common drive mechanism (not illustrated). The inlets 27 are connected with an inflow 30 of the coupling piece 29. The outlets 28 are connected with an outflow (not shown) of the coupling piece 29. Referring to FIG. 5, coupling piece 29 is arranged in a gap 45 in the cover 22 which is open on the side of cover 22 opposite to the side where the hinge 34 is located.

As is evident from FIG. 4, the two swash plates 20 have a relative phase shift of 180°. While the left swash plate 20 executes the strongest pinching of the respective hose 26 on the side adjacent to the coupling piece 29, the right swash plate 20 causes maximum pinching at the same moment at the point of the respective hose 26 farthest away from or remote from the coupling piece 29.

In the embodiment of the invention illustrated in FIGS. 4 and 5, the cover 22 receives the two hoses 26, which jointly lie in a common plane. Together with the coupling piece 29 arranged between them, the hoses 26 form a disposable unit. Because of the phase-shifted drive of the two swash plates 20, any discontinuities in time of the total delivery of the hose pump are diminished.

It will be readily appreciated that the details of construction of the right and left swash plates 20 and associated mechanisms of the embodiment of FIG. 4 may be suitably substantially similar to the details illustrated and described in conjunction with the embodiment of FIG. 1.

Although preferred embodiments of the present invention have been described in detail, it is contemplated that modifications may be made within the spirit and the scope of the invention.

What is claimed is:

1. In a hose pump for medical uses comprising a housing, a drive shaft mounted in said housing, a shaft piece joined to and extending obliquely away from said drive shaft, a swash plate mounted on said shaft piece, means for substantially non-rotationally retaining said swash plate relative to said housing, a cover disposed on said housing with said cover having a first end and a second end and an underside which faces said swash plate with said cover in the closed position, the improvement comprising:

means formed on the underside of said cover for receiving an annular hose section;

hinge means connected to said first end of said cover for pivotally mounting said cover to said housing;

locking means located near said second end of said cover for locking said cover to said housing in the closed position; and means located at said second end of said cover for receiving a hose coupling piece.

2. A hose pump as recited in claim 1 wherein said means for receiving said annular hose section comprises an annular groove formed on the underside of said cover and clamping means mounted on the underside of said cover for securing said hose in said annular groove.

3. A hose pump as recited in claim 1 further including:

an annular hose section having an inlet end and an outlet end disposed in said receiving means of said cover wherein said hose section is pressed between said swash plate and said underside of said cover with said cover in the closed position; and a common hose coupling piece inserted in said hose coupling piece receiving means with said hose inlet end and outlet end connected in fluid communication with said common coupling piece.

4. A hose pump as recited in claim 3 wherein said common hose coupling piece has a generally L-shaped angle shape with the first leg of said angle extending under said cover and the second leg of said angle projecting upward through said hose coupling piece receiving means and terminating above the top side of said cover.

5. A hose pump as recited in claim 2 wherein said swash plate comprises a ring-like member having a top face protruding into said annular groove with said cover in the closed position.

6. A hose pump as recited in claim 3 wherein said receiving means of said cover comprise an annular groove formed on the underside of said cover and said swash plate comprises a ring-like member having a top face protruding into said annular groove with said cover in the closed position wherein said swash plate pinches said hose at a selected location and wherein the width of said annular groove approximately corresponds to the width of the pinched hose.

7. A hose pump as recited in claim 5 wherein the mean diameter of said annular groove is approximately the same as the mean diameter of said top face of said swash plate.

8. A hose pump as recited in claim 6 wherein the mean diameter of said annular groove is approximately the same as the mean diameter of said top face of said swash plate pressing against said hose.

9. A hose pump as recited in claim 7 wherein the axis of said drive shaft and the axis of said shaft piece intersect at a point which is located approximately in the plane of the mean diameter of said top face of said swash plate.

10. A hose pump as recited in claim 8 wherein the axis of said drive shaft and the axis of said shaft piece intersect at a point which is located approximately in the plane of the mean diameter of said top face of said swash plate.

11. A hose pump as recited in claim 5 wherein:
said housing has a cavity defined by an inner wall of said housing for receiving said swash plate;
said swash plate is disposed in said cavity;
said swash plate has a circumferential side wall; and,
a membrane member is sealingly joined to said swash plate sidewall and said housing inner wall.

12. A hose pump as recited in claim 6 wherein:
said housing has a cavity defined by an inner wall of said housing for receiving said swash plate;
said swash plate is disposed in said cavity;
said swash plate has a circumferential side wall; and,
a membrane member is sealingly joined to said swash plate sidewall and said housing inner wall.

13. A hose pump for medical uses comprising:
a housing having a first section and an adjacent second section;
a first drive shaft mounted in said housing first section, a first shaft piece joined to and extending obliquely away from said first drive shaft, a first swash plate mounted on said first shaft piece, means for substantially non-rotationally retaining said first swash plate relative to said housing;
a second drive shaft mounted in said housing second section, a second shaft piece joined to and extending obliquely away from said second drive shaft, a second swash plate mounted on said second shaft piece, means for substantially non-rotationally retaining said second swash plate relative to said housing;
wherein said first and second swash plates are arranged side by side;
a cover mounted on said housing having an underside facing said first and second swash plate with said cover in the closed position, wherein said cover underside facing said first and second swash plate substantially lies in a common plane; and
drive means for driving said first and second swash plates at equal speeds.

14. A hose pump as recited in claim 13 further including:
a first annular hose section having an inlet and an outlet pressed between said first swash plate and the underside of said cover with said cover in the closed position;
a second annular hose section having an inlet and an outlet pressed between said second swash plate and the underside of said cover with said cover in the closed position;
wherein said first and second hose sections substantially lie in a common plane; and
a common hose coupling piece connected in fluid communication with the inlet and outlet of said first hose section and the inlet and outlet of said second hose section wherein said common hose coupling piece has a single inflow and a single outflow.

15. A hose pump as recited in claim 13 wherein said cover is hingedly mounted to said housing.

16. A hose pump as recited in claim 13 wherein the underside of said cover has a first annular groove for receiving a first annular hose section and a second annular groove for receiving a second annular hose section:
said first swash plate is a ring-like member having a top face protruding into said first annular groove with said cover in the closed position;
said second swash plate is a ring-like member having a top face protruding into said second annular groove with said cover in the closed position.

17. A hose pump as recited in claim 13 wherein the plane of the top face of said first swash plate is arranged with respect to the plane of the top face of said second swash plate whereby, upon rotation of said first and second drive shafts by said drive means, said first and second swash plates are driven in phase opposition.

18. A hose pump as recited in claim 14 wherein the plane of the top face of said first swash plate is arranged with respect to the plane of the top face of said second swash plate whereby, upon rotation of said first and second drive shafts by said drive means, said first and second swash plates are driven in phase opposition.

19. A hose pump as recited in claim 16 wherein the plane of the mean diameter of said first swash plate top face is approximately parallel to the plane of the mean diameter of said second swash plate top face whereby, upon rotation of said first and second drive shafts by said drive means, said first and second swash plates are driven in phase opposition.

20. A hose pump as recited in claim 16 further including:
a first annular hose section having an inlet and outlet disposed in said first annular groove and pressed between said first swash plate top face and said underside of said cover with said cover in the closed position;
a second annular hose section having an inlet and outlet disposed in said second annular groove and pressed between said second swash plate top face and said underside of said cover with said cover in the closed position; and
a common hose coupling piece connected in fluid communication with the inlet and outlet of said first hose section and with the inlet and outlet of said second hose section wherein said common hose coupling piece has a single inflow and a single outflow.

21. A hose pump as recited in claim 19 further including:
a first annular hose section having an inlet and outlet disposed in said first annular groove and pressed between said first swash plate top face and said underside of said cover with said cover in the closed position;
a second annular hose section having an inlet and outlet disposed in said second annular groove and pressed between said second swash plate top face and said underside of said cover with said cover in the closed position; and a common hose coupling piece connected in fluid communication with the inlet and outlet of said first hose section and to the inlet and outlet of said second hose section wherein said common hose coupling piece has a single inflow and a single outflow.

* * * * *